(12) United States Patent
Fengler et al.

(10) Patent No.: US 6,211,417 B1
(45) Date of Patent: Apr. 3, 2001

(54) PROCESS FOR PREPARING BIS-(4-HYDROXYARYL) ALKANES

(75) Inventors: Gerd Fengler; Hans-Josef Buysch, both of Krefeld; Frieder Heydenreich, Düsseldorf, all of (DE); Rob Eek, Bergen op Zoom (NL); Gerhard Fennhoff, Stabroek (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/341,506

(22) PCT Filed: Jan. 7, 1998

(86) PCT No.: PCT/EP98/00034

§ 371 Date: Aug. 9, 1999

§ 102(e) Date: Aug. 9, 1999

(87) PCT Pub. No.: WO98/31651

PCT Pub. Date: Jul. 23, 1998

(30) Foreign Application Priority Data

Jan. 16, 1997 (DE) ............................................. 197 01 278

(51) Int. Cl.[7] .................................................. C07C 39/16
(52) U.S. Cl. ............................................ 568/728; 568/727
(58) Field of Search ..................................... 568/727, 728

(56) References Cited

U.S. PATENT DOCUMENTS

| 2,775,620 | 12/1956 | Williamson | 260/619 |
|---|---|---|---|
| 4,301,305 | * 11/1981 | Kiedik | 568/727 |
| 4,391,997 | 7/1983 | Mendiratta | 568/727 |
| 4,400,555 | 8/1983 | Mendiratta | 568/728 |
| 4,859,803 | 8/1989 | Shaw | 568/727 |

FOREIGN PATENT DOCUMENTS 0 754 666   1/1997   (EP) .

* cited by examiner

*Primary Examiner*—Michael L. Shippen
(74) *Attorney, Agent, or Firm*—Joseph C. Gil; Aron Preis

(57) ABSTRACT

The present invention relates to a process for the production of bis-(4-hydroxyaryl)-alkanes by a heterogeneously catalyzed reaction of aromatic hydroxy compounds with ketones in at least two reactors connected in series, which, as the reaction progresses, are operated at higher temperatures, wherein the total quantity of ketone is divided between the individual reactors in such a manner that the higher is the temperature of the particular reactor, the smaller is the proportion per reactor, the highest possible reactor loading is maintained and the temperatures and temperature gradients are kept as low as possible.

3 Claims, 1 Drawing Sheet

PROCESS FOR PREPARING BIS-(4-HYDROXYARYL) ALKANES

The present invention relates to a process for the production of bis-(4-hydroxyaryl)-alkanes by a heterogeneously catalysed reaction of aromatic hydroxy compounds with ketones in reactors connected in series, which, as the reaction progresses, are operated at higher temperatures, wherein the total quantity of ketone is divided between the individual reactors in such a manner that the higher is the temperature of the particular reactor, the smaller is the quantity.

It is known to divide the required quantity of ketone between two or more reactors connected in series in a process for the production of bis-(4-hydroxyaryl)alkanes from phenols and ketones. U.S. Pat. No. 2,775,620 describes a homogeneous liquid phase process catalysed with mineral acid, while a heterogeneously catalysed process with an acidic ion exchanger in a fixed bed reactor is disclosed in U.S. Pat. No. 4,400,555 (EP-A 342 758). Both documents show that dividing the quantity of ketone reduces the proportion of secondary products, wherein this quantity is lower with HCl catalysis than with ion exchanger catalysis.

Catalysis of the reaction with HCl differs distinctly from catalysis with heterogeneous catalysts both chemically and with regard to processing. As a rule, HCl catalysis is more selective and may moreover be performed at lower temperatures as crystallisation in the reactors can be tolerated or is even advantageous in order to achieve higher selectivity. In U.S. Pat. No. 2,775,620, the process is thus operated at substantially below the crystallisation temperature of 63° C. and high selectivity is achieved. This is quite different from U.S. Pat. No. 4,400,555, where the temperature is maintained at 67° C. in order to prevent crystallisation and thus clogging of the (heterogeneous) catalyst bed. In the Examples, the process is operated at an acetone conversion of 66%. The increase in selectivity is distinctly less than in the HCl catalysed reaction. It is moreover established that selectivity rises further if the larger quantity of acetone is introduced into the second reactor.

The improvement in selectivity for bis-(4-hydroxyaryl) alkanes found according to U.S. Pat. No. 4,400,555 is still inadequate. It is thus desirable to develop processes in which, under the conditions of a continuously operated plant, the smallest possible quantities of isomers and especially secondary products are formed.

It has now been found that distinctly higher selectivities for bis-(4-hydroxyaryl)alkanes are obtained if the total quantity of ketone is divided between the reactors in such a manner that less ketone is apportioned to the individual reactor, the higher the temperature of the reactor is, reactor loading is as high as possible and, while temperature does indeed rise along the series of reactors, it is kept comparatively as low as possible.

The present invention accordingly provides a process for the production of bis-(4-hydroxyaryi)alkanes by a heterogeneously catalysed reaction of aromatic hydroxy compounds with ketones in at least two reactors connected in series, which, as the reaction progresses, are operated at higher temperatures, wherein the total quantity of ketone is divided between the individual reactors in such a manner that the higher is the temperature of the particular reactor, the smaller is the proportion per reactor.

Suitable aromatic hydroxy compounds for the process according to the invention are not substituted in p-position and contain no second order substituents such as cyano, carboxy or nitro groups; the following may be mentioned by way of example, phenol, o- and m-cresol, 2,6-dimethylphenol, o-tert.-butylphenol, 2-methyl-6-tert.-butylphenol, o-cyclohexylphenol, o-phenylphenol, o-isopropylphenol, 2-methyl-6-cyclopentylphenol, o- and m-chlorophenol, 2,3,6-trimethylphenol. Phenol, o- and m-cresol, 2,6-dimethylphenol, o-tert.-butylphenol and o-phenylphenol are preferred; phenol is particularly preferred.

Suitable ketones contain at least one aliphatic group on the carbonyl function; the following may be mentioned by way of example, acetone, methyl ethyl ketone, methyl propyl ketone, methyl isopropyl ketone, diethyl ketone, acetophenone, cyclohexanone, cyclopentanone, methyl-, dimethyl- and trimethylcyclohexanone, which may also have germinal methyl groups, such as 3,3,-dimethyl-5-methylcyclo-hexanone (hydroisophorone). Acetone, acetophenone, cyclohexanone and the homologues thereof bearing methyl groups are preferred; acetone is particularly preferred.

The molar ratio of aromatic hydroxy compound to ketone is generally 5:1 to 25:1, preferably 7:1 to 20:1, particularly preferably 8:1 to 18:1, relative to the complete reaction.

The educt mixture used may contain small quantities of water, preferably less than 1, particularly preferably less than 0.6 and very particularly preferably less than 0.3 wt. %.

The ion exchange resins used as catalysts and the mercapto compounds used as cocatalysts are known to the person skilled in the art (U.S. Pat. No. 2,468,982, 2,623,908; 2,775,620; DE-OS 36 19 450; 37 27 641).

The reactors number at least two and, for reasons of economic viability, will not generally number more than eight, preferably no more than six, particularly preferably no more than four.

The quantity of ketone is divided between the reactors in such a manner that the quantity per reactor decreases as the reactor temperature increases. If there are two reactors, 60 to 90%, preferably 65 to 85% are introduced into the first reactor, while if there are three reactors, 40 to 80%, preferably 50 to 70% are introduced into the first reactor and 10 to 40%, preferably 15 to 35% into the second reactor and the remainder into the third reactor.

Loading, defined as the quantity of educt mixture (in kg) per litre of catalyst in the operating state (swollen) per hour, per reactor is 0.2 to 2.0, preferably 0.3 to 1.7, particularly preferably 0.4 to 1.5 kg/l·h. The loading should generally be selected such that, after the last reactor, acetone conversion is at least 75%, better $\geq 80\%$, preferably $\geq 85\%$.

It is not necessary to operate all the reactors at the same loading. Instead, it may be advantageous, in order further to increase selectivity, to increase reactor loading from reactor to reactor as conversion increases. For example, in a plant having three reactors, the first reactor may be operated at 0.3, the second reactor at 0.6 and the third reactor at 0.8 kg/l·h.

In order to achieve an effective reduction in the quantity of by-products, it is very important that the ketone is entirely homogeneously distributed in the reaction mixture before it passes into the catalyst bed, which may be achieved by using nozzles, static mixers, stirred tanks, centrifugal pumps or other mixing apparatus familiar to the person skilled in the art.

The reactors connected in series are operated at higher temperatures as the reaction progresses. A rising temperature profile of 35 to 85° C., preferably of 38 to 75° C., particularly preferably of 40 to 70° C., very particularly preferably of 42 to 68° C. is established between the beginning and the end of the series of reactors. The temperature differences between one reactor and the next will generally be smaller, the greater is the number of reactors the mixture is to pass through. It is also possible to operate two successive reactors at the same temperature.

Since no mixing occurs in fixed bed reactors and it is difficult to dissipate the heat of reaction from the reaction mixture, such reactors are generally operated adiabatically, which results in heating of the reaction mixture. It is thus usually convenient to cool the reaction mixture between the individual reactors, wherein care must be taken to ensure that any crystallisation of bis-(4-hydroxyaryl)alkane, which would block the lines, is avoided.

BRIEF DESCRIPTION OF DRAWING

A schematic diagram of the test setup is shown in FIG. 1.

EXAMPLES

Figure 1:
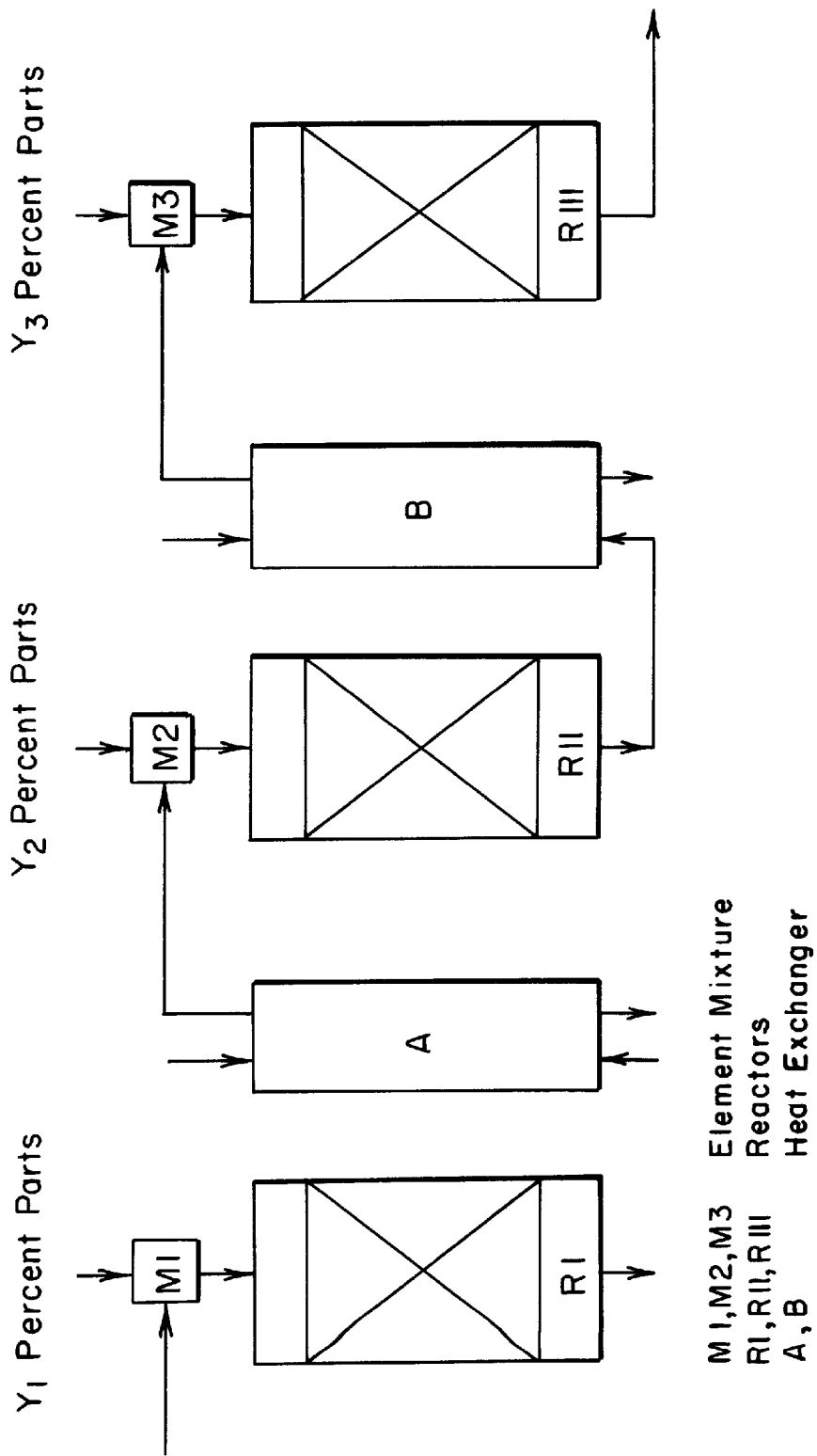

A mixture of $100-Y_1-0.2$ wt. % of phenol, $Y_1$ wt. % of acetone and 0.2 wt. % of water is charged at a temperature, depending upon the Example, of 45 to 56° C. and a loading of 0.2 to 0.8 kg/l·h under $N_2$ through the catalyst bed in the first of a series of three fixed bed reactors connected in series and filled with a sulphonated styrene resin crosslinked with 2 wt. % of divinylbenzene and laden with 3.5 wt. % of cysteamine.

The product mixture leaving the reactor was mixed with $Y_2$ parts by weight of acetone and passed through the second catalyst bed at 51 to 68° C., depending upon the Example, and a loading of 0.2 to 0.8 kg/l·h.

$Y_3$ parts by weight of acetone were mixed into the product mixture discharged from the second reactor and passed through the third reactor at 51 to 76° C. and 0.2 to 0.8 kg/l·h.

Acetone conversion was U%. Each Example was performed for some hundreds of hours. Table 1 shows the averaged composition obtained by daily analysis of the reaction mixtures after the third reactor.

TABLE 1

| No. | Loading | Acetone division, wt. % | | | Temperature, °C. | | | Acetone conversion U% | Bisphenol A % | o, o'-bis-phenol % | o, p'-bis-phenol % | Chromanes % | Indanes % |
| --- | --- | --- | --- | --- | --- | --- | --- | --- | --- | --- | --- | --- | --- |
|  |  | $Y_1$ | $Y_2$ | $Y_3$ | R.I | R.II | R.III |  |  |  |  |  |  |
| 1 | 0.2 | 2.0 | 1.3 | 0.6 | 54 | 64 | 74 | 100 | 93.34 | 0.09 | 5.75 | 0.14 | 0.10 |
| a* | 0.2 | 1.3 | 1.3 | 1.3 | 54 | 64 | 74 | 99.8 | 92.83 | 0.10 | 6.10 | 0.27 | 0.22 |
| b* | 0.2 | 3.9 | 0 | 0 | 74 | — | — | 100 | 91.70 | 0.14 | 6.65 | 0.53 | 0.25 |
| 2 | 0.6 | 2.0 | 1.3 | 0.6 | 56 | 68 | 76 | 99.8 | 94.47 | 0.07 | 4.89 | 0.09 | 0.03 |
| c* | 0.6 | 1.3 | 1.3 | 1.3 | 54 | 64 | 74 | 98.8 | 93.16 | 0.10 | 5.87 | 0.21 | 0.18 |
| 3 | 0.8 | 2.0 | 1.3 | 0.6 | 56 | 68 | 76 | 94.2 | 95.18 | 0.07 | 4.13 | 0.08 | 0.07 |
| 4 | 0.6 | 2.0 | 1.3 | 0.6 | 50 | 59 | 63 | 98.1 | 96.10 | 0.06 | 3.27 | 0.08 | 0.02 |
| 5 | 0.6 | 2.0 | 1.3 | 0.6 | 45 | 51 | 57 | 95.3 | 96.95 | 0.04 | 2.65 | 0.06 | 0.02 |

*Comparative Example

The lowest selectivity for bisphenol A (BPA) is achieved when the acetone is not divided (Comparison b). If the same quantity of acetone is used, but divided equally between three reactors (R.I, R.ll, R.III) (Comparison a), and a temperature gradient is simultaneously applied to the series of reactors, BPA selectivity increases. Finally, if the quantity of acetone is divided according to the invention between the reactors in such a manner that the proportion per reactor falls as temperature rises, a further increase in selectivity is to be observed under otherwise identical conditions. If catalyst loading is increased, BPA selectivity is further improved. Reducing the temperature gradient produces still better selectivities.

It may thus be concluded that BPA selectivity increases with a non-uniform division of acetone, in which reactor I receives the largest proportion, reactor II a moderate proportion and reactor III, having the highest temperature, the smallest proportion, if the temperature and temperature gradient are kept as low as possible and the highest possible reactor loading is maintained.

In contrast, according to U.S. Pat. No. 4,400,555, higher BPA selectivity is achieved in a process with two reactors operated at identical temperature if the larger part of the quantity of acetone is apportioned into the second reactor.

What is claimed is:
1. Process for the production of bis-(4-hydroxyaryl) alkanes by a heterogeneously catalysed reaction of aromatic hydroxy compounds with ketones in at least two reactors connected in series, which, as the reaction progresses, are operated at higher temperatures, wherein the total quantity of ketone is divided between the individual reactors in such a manner that the higher is the temperature of the particular reactor, the smaller is the proportion per reactor.

2. Process according to claim 1, in which the loading of the reactors is 0.2 to 2.0 kg/l·h.

3. Process according to claim 1, in which the reactor temperatures are 35 to 85° C.

* * * * *